(12) United States Patent
Lanzendörfer et al.

(10) Patent No.: US 6,562,794 B1
(45) Date of Patent: *May 13, 2003

(54) COSMETIC AND DERMATOLOGICAL FORMULATIONS COMPRISING FLAVONOIDS

(75) Inventors: Ghita Lanzendörfer, Hamburg (DE); Franz Stäb, Echem (DE); Sven Untiedt, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/540,007

(22) Filed: Mar. 30, 2000

Related U.S. Application Data

(62) Division of application No. 08/849,524, filed as application No. PCT/EP95/04905 on Dec. 12, 1995, now Pat. No. 6,121,243.

(30) Foreign Application Priority Data

Dec. 13, 1994 (DE) .......................................... 44 44 238

(51) Int. Cl.$^7$ .......................... A61K 31/70; A61K 7/42; A61K 7/44
(52) U.S. Cl. ............................ 514/28; 424/59; 424/60; 424/70.9
(58) Field of Search ............................ 514/28; 424/59, 424/60, 70.9

(56) References Cited

U.S. PATENT DOCUMENTS 5,652,266 A * 7/1997 Bobier-Rival et al. ...... 514/557
5,925,363 A * 7/1999 Colin et al. .................. 424/401

FOREIGN PATENT DOCUMENTS

| EP | 387042 | 9/1990 |
| EP | 402049 | 12/1990 |
| EP | 496649 | 7/1992 |
| EP | 595694 | 5/1994 |
| GB | 2259014 | 3/1993 |

OTHER PUBLICATIONS

"DC Studies of Flavoniod Patterns of the Five Pharmacopoeial Species", English translation of Schüssler, Monika and Hölzl, Josef, Deutsche Apotheker Zeitung, 132, Nr. 25 (1992), pp. 1327–1329.

"Extracts from Medicinal Plants Used in Cosmetics", English translation of Bergwein K.: Extrakte aus Heilkräutern in der Kosmetik. In: Seifen–Öle–Fette–Wachse, 1968, Jg. 94, No. 25, pp. 885–886.

"Ferulic Acid", English translation of Dr. Fiedler H.P., In: Lexikon der Hilfsstoffe für Pharmazie, Kosmetik und angrenzende Gebiete, Aulendorf: Editio Cantor, 1981, p. 386.

Patent Abstract of Japan, vol. 12, No. 496, JP 63–208506, dated Dec. 23, 1988.

Patent Abstract of Japan, vol. 13, No. 308, JP 01–096106, dated Jul. 14, 1989.

Schüssler, Monika and Hölzl, Josef, Deutsche Apotheker Zeitung, 132, Nr. 25 (1992), pp. 1327–1329.

Vennat, B., Gross, D.; Pourrat, A.; Pourrat, H.; Pharm. Acta Hebr. 67, Nr. 1 (1992), pp. 11–14.

Broussalis, A.M., Ferrarao, G.E., et al.; Biochem. Syst. Ecol., 16, Nr. 4, (1988), pp. 401–402.

Fraga, Cesar E., Martino, Virginia S., et al.: Biochem. Parmacol., 36, Nr. 5 (1987), pp. 719–720.

Chem. Abstract 120: 226663b (1994).
Chem. Abstract 107: 205272q (1987).
Chem. Abstract 97: 123964c (1982).
Chem. Abstract 71: 64044r (1969).
Chem Abstract 112: 135978b (1990).

Bergwein K.: Extrakte aus Heilkräutern in der Kosmetik. In: Seifen–Öle–Fette–Wachse, 1968, Jg. 94, No. 25, pp. 885–886.

Dr. Fiedler H.P., In: Lexikon der Hilfsstoffe für Pharmazie, Kosmetik und angrenzende Gebiete, Aulendorf: Editio Cantor, 1981, p. 386.

* cited by examiner

Primary Examiner—Rebecca Cook
(74) Attorney, Agent, or Firm—Norris McLaughlin & Marcus

(57) ABSTRACT

The invention relates to cosmetic and dermatological formulations having a) a content of a compound or several compounds from the group consisting of flavonoids, or having b) a content of an active compound combination comprising a compound or several compounds chosen from the group consisting of flavonoids in combination with a compound or several compounds chosen from the group consisting of cinnamic acid derivatives and c) if appropriate an additional content of a compound or several compounds from the group consisting of antioxidants.

2 Claims, No Drawings

COSMETIC AND DERMATOLOGICAL FORMULATIONS COMPRISING FLAVONOIDS

This is a division of Ser. No. 08/849,524 filed Apr. 8, 1997 now U.S. Pat. No. 6,121,243 which is a 371 of PCT/EP45/04905 filed Dec. 12, 1995.

The present invention relates in particular to cosmetic and dermatological formulations comprising flavonoids, their glycosides and, if appropriate, combinations thereof with cinnamic acid derivatives or antioxidants.

The damaging effect of the ultraviolet component of solar radiation on the skin is generally known. While rays having a wavelength below 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as the maximum for the erythema activity of sunlight.

Numerous compounds which are derivatives of 3-benzylidenecamphor, of 4-aminobenzoic acid, of cinnamic acid, of salicylic acid, of benzophenone and also of 2-phenylbenzimidazole are known for protection against UVB radiation.

It is also important to have filter substances available for the range between about 320 nm and about 400 nm, the so-called UVA range, since rays in this range can cause reactions on photosensitive skin. It has been proved that UVA radiation leads to damage to the elastic and collagenic fibres of connective tissue, which causes the skin to age prematurely, and that it is to be regarded as a cause of numerous phototoxic and photo-allergic reactions. The damaging influence of UVB radiation may be intensified by UVA radiation.

Certain derivatives of dibenzoylmethane are therefore used for protection against the rays of the UVA range, the photostability of which derivatives (Int. J. Cosm. Science 10, 53 (1988)) is not adequate.

However, UV radiation can also lead to photochemical reactions, the photochemical reaction products then intervening in skin metabolism.

Such photochemical reaction products are chiefly free-radical compounds, for example hydroxyl radicals. Undefined free-radical photo-products which are formed in the skin itself can also show uncontrolled secondary reactions because of their high reactivity. However, singlet oxygen, a non-radical excited state of the oxygen molecule, may also occur under UV irradiation, as may short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in biochemical processes.

To prevent these reactions, additional antioxidants and/or free-radical scavengers can be incorporated into the cosmetic or dermatological formulations.

It has already been proposed to employ vitamin E, a substance of known antioxidative action, in light protection formulations, although here too the effect achieved falls far short of that hoped for.

The effect of solar radiation on the skin, apart from the development of photo-weals and tanning, caused chiefly by the UVB range, is a slow and progressive degradation of the connective tissue lying underneath the epidermis, caused by the longer-wavelength range of sunlight, the UVA, in which the elastic and strengthening fibres are destroyed by irradiation. The decreasing strength of the connective tissue leads to increased formation of wrinkles, and in the extreme case can lead to so-called "farmer's skin" or even actinic keratosis. Wrinkles, ruga and dry skin which form due to environmental influences before the actual biological age and are the symptom of "premature ageing of the skin" are regarded as cosmetically undesirable.

Antioxidants are chiefly used as protective substances against the decay of the formulations comprising them. Nevertheless, it is known that undesirable oxidation processes can also occur in human and animal skin. Such processes play an essential role in ageing of the skin.

Oxidative damage to the skin and its more detailed causes are described in the paper "Skin Diseases Associated with Oxidative Injury" in "Oxidative Stress in Dermatology", page 323 et seq. (Marcel Decker Inc., New York, Basle, Hong Kong, editors: Jurgen Fuchs, Frankfurt, and Lester Packer, Berkeley/Calif.).

The object of the invention was therefore to provide cosmetic and dermatological active compounds and formulations and light protection formulations which are used for prophylaxis and treatment of light-sensitive skin, and also of normal skin exposed to the sun.

The lips are furthermore an area of the face which, due to its structure and exposure, is severely subjected to and influenced by external influences. The naturally red colour of the lips is based on the fact that the skin of the lips is much thinner than "normal" skin and sweat and sebaceous glands are also absent. Melanine is present to a significantly lesser degree. The absence of some of the natural protection of the skin means that lips are exposed to greater stresses than normal skin under cold temperatures, heat and solar radiation. Protection and care of the lips are therefore necessary to obtain a smooth, rosy appearance of the lips. If no adequate protection of the lips has been present during exposure, the abovementioned symptoms manifest themselves, alleviation and elimination of which can also be regarded as a cosmetic concern.

The invention moreover relates to formulations of extremely low so-called "stinging potential" and formulations for non-specific, non-pathological itching.

As a barrier organ of the human organism, the skin, especially the epidermis, is subjected to external effects to a considerable extent. According to current scientific understanding, the skin represents an immunological organ which, as an immunocompetent peripheral compartment, plays its own role in inductive, effective and regulatory immune processes of the entire organism.

The epidermis is richly equipped with nerves and peripheroceptors, such as Vater-Pacini lamellated corpuscles, Merkel cell-neurite complexes and free nerve endings for sensation of pain, cold and heat and itching.

In humans with delicate, sensitive or vulnerable skin, a neurosensory phenomenon called "stinging" ("sting"= injure, burn, hurt) can be observed. This "delicate skin" differs fundamentally from "dry skin" with thickened and hardened horny layers.

Typical reactions of "stinging" on delicate skin are reddening, tightening and burning of the skin and itching.

Typical disturbing neurosensory phenomena associated with the terms "stinging" or "sensitive skin" are reddening of the skin, tingling, prickling, tightening and burning of the skin and itching. They can be caused by stimulating ambient conditions, for example massage, action of surfactants, influence of weather such as sun, cold, dryness and also damp heat, thermal radiation and UV radiation, for example from the sun.

In "Journal of the Society of Cosmetic Chemists" 28, pages 197–209 (May 1977) P. J. Frosch and A. M. Kligman describe a method for estimating the "stinging potential" of substances applied topically. Positive substances employed here are, for example, lactic acid and pyruvic acid. However, amino acids, in particular glycine, have also been determined as having a neurosensory action (such substances are called "stingers") when measured by this method.

According to findings to date, such a sensitivity towards quite specific substances occurs to different degrees in individuals. This means that a person who experiences "stinging effects" in contact with a substance will with high probability experience them repeatedly on each further contact. However, contact with other "stingers" can equally take place without any reaction.

Itching on atopic skin is to be regarded as a neurosensory phenomenon, as is itching with skin diseases, although this is only a symptom of these diseases but conversely can also develop non-specifically, i.e. without a clinical finding of a disturbance of the skin, infection or irritation. Although non-specific itching is also a first indication of a possible masked general disease, it can also be caused by stress or other environmental influences.

Itching without a clearly recognizable reason can furthermore occur, preferentially on rather sensitive persons.

"Stinging" phenomena can thus be regarded generally as disturbances to be treated cosmetically. More severe itching, on the other hand, especially severe itching of the skin occurring with atopy, can also be described as a more serious dermatological disturbance, while itching which occurs with stinging or non-specifically without a disease can also be regarded as a disturbance to be treated cosmetically.

The problem of sensitive or delicate skin is furthermore increasing ever more. This is on the one hand often characterized by an increased susceptibility to stinging, but is also characterized by other criteria, such as: skin which tends to go red, skin of-photo type I or II, known allergy, a basic dermatological disease, such as atopic dermatitis or psoriasis, known intolerances to cosmetic products, the subjective feeling of a lack of oil and moisture content of the skin.

For further characterization of sensitive skin, a "permeable" barrier which manifests itself in an increased TEWL is discussed. Products having an occlusive action or lipid-substituting products which lower the TEWL after application are recommended for barrier regeneration. P. Elias even describes various lipid mixtures which have the effect of barrier regeneration on the skin of mice which has been predamaged with acetone. Topical application of RRR-a-tocopherol also detectably improves the skin barrier.

If human hair is to be coloured permanently, only oxidizing hair colouring methods are suitable in practice. During oxidative colouring of the hair, the dyestuff chromophore is formed by reaction of precursors (phenols, aminophenols, less frequently also diamines) and bases (usually p-phenylenediamine) with the oxidizing agent, usually hydrogen peroxide. Hydrogen peroxide concentrations of about 6% are usually used here.

It is usually assumed that, in addition to the colouring action, a bleaching action also occurs due to the hydrogen peroxide. In oxidatively coloured human hair, as in bleached hair, microscopic holes are detectable at the places where melanine granules were present.

The fact is that the oxidizing agent hydrogen peroxide can react not only with the colour precursors but also with the hair substance and under certain circumstances can cause damage to the hair as a result.

Derivatives of thioglycolic acid, which reduces the S—S bond of keratin and therefore renders deformation of the hair possible, are employed for permanent wave treatment of hair. The S—S bonds must subsequently be closed again by a so-called fixer so that the deformation is retained. Permanent wave treatment takes place in an alkaline, neutral or acid medium, in which the hair and scalp swell and react very sensitively.

It is furthermore known that the scalp is also influenced during the colouring process as well as during permanent waving. The skin keratin is attacked in the same way as the hair keratin. The skin of the hands can also be influenced, since in spite of recommended safety precautions from the manufacturers of these products, gloves are not worn or the hands nevertheless come into contact with the dyes or permanent wave liquid when these are rinsed out.

The hair and scalp are furthermore a part of the body which, because of its position, is exposed to a considerable proportion of UV radiation during periods in the open. To date there have been only a few products which take into account protection of the hair. Products which are applied to the hair and scalp after exposure to light, alleviate the adverse effects and thus keep the hair shiny and smooth and prevent or alleviate dandruff are unknown.

Antioxidants are substances which prevent oxidation processes or which prevent the autooxidation of fats containing unsaturated compounds. Antioxidants which are also used in the fields of cosmetics and pharmaceuticals are, for example, α-tocopherol, in particular in the form of α-tocopheryl acetate, sesame oil, bile acid derivatives, butylhydroxyanisole and butylhydroxytoluene.

Antioxidants and/or free-radical scavengers can also additionally be incorporated into cosmetic formulations in order to prevent such reactions.

Some antioxidants and free-radical scavengers are indeed known. It has thus already been proposed in U.S. Pat. No. 4,144,325 and 4,248,861 and from numerous other documents to employ vitamin E, a substance of known antioxidative action, in light protection formulations, but here also the effect achieved falls far short of that hoped for.

An object of the present invention was to eliminate the disadvantages of the prior art. In particular, active compounds or formulations comprising such active compounds which, when used, can at least reduce, if not prevent entirely, damage to the skin and/or hair caused by an oxidative influence were to be provided.

Another object of the present invention was to provide cosmetic formulations which, before or after treatment of the hair with hair colour formulations or permanent wave products, even those having a content of potent oxidizing agents, such as, for example, hydrogen peroxide, counteract the damaging oxidizing action thereof.

In particular, active compounds and formulations comprising such active compounds for cosmetic and dermatological treatment and/or prophylaxis of the clinical picture of "stinging" were to be provided.

It was surprising and was not to be foreseen by the expert that formulations and active compound combinations according to the invention comprising active amounts of substances chosen from the group consisting of flavonoids or their glycosides by themselves or their combination with substances from the group consisting of cinnamic acid derivatives or hydroxycinnamic acids remedy the disadvantages of the prior art.

The above objects are achieved according to the invention.

The invention relates to cosmetic and dermatological formulations having
a) a content of a compound or several compounds from the group consisting of flavonoids, or having
b) a content of an active compound combination comprising a compound or several compounds chosen from the group consisting of flavonoids in combination with a compound or several compounds chosen from the group consisting of cinnamic acid derivatives and
c) if appropriate an additional content of a compound or several compounds from the group consisting of antioxidants.

Active compound combinations b), their use and formulations which comprise these are preferred.

Topical formulations are preferred.

The flavonoids according to the invention are also designated A) below, the cinnamic acid derivatives according to the invention are also designated B) and the antioxidants according to the invention are also designated C).

Preferred flavonoids according to the invention are, for example, hydroxylated flavones, flavanones, isoflavones or chalcones, and in each case also glycosides thereof, and also these non-hydroxylated base structures or parent substances.

According to the invention, the flavonoids A) are preferably chosen from the group of substances having the generic structural formulae

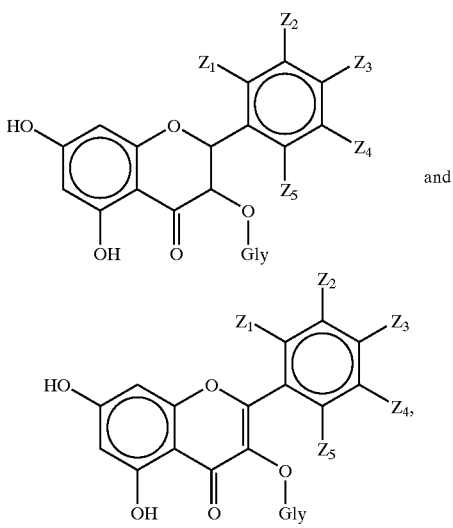

wherein $Z_1$–$Z_5$ independently of one another are chosen from the group consisting of H, OH and O-alkyl, wherein the alkyl groups can be branched and unbranched and can contain 1–18 C atoms, and wherein Gly is chosen from the group consisting of mono-, di- and oligoglycoside radicals or can also be H. Radicals Gly can be, for example, the radicals mentioned for Gly1–Gly3. Radicals Gly can be, for example, the radicals mentioned for $Gly_1$–$Gly_3$.

It is advantageous in the context of the present invention to choose the flavonoid or flavonoids A) from the group consisting of quercitin, chrysin, kaempferol, myricetin, apigenin, naringenin, hesperitin, morin, fisetin, vitexin, isovitexin, flavone and genistein.

It is also advantageous to choose the flavone glycosides A) from the group consisting of rutin, rhamnetin, luteolin, naringin, hesperidin, phloridzin, diosmin and neohesperidin dihydrochalcone.

Chrysin, naringin, hesperidin, naringenin, hesperetin, morin, phloridzin, diosmin, neohesperidin dihydrochalcone and flavone are particularly preferred.

Further flavonoids A) according to the invention are advantageously chosen from the group of substances having the generic structural formulae:

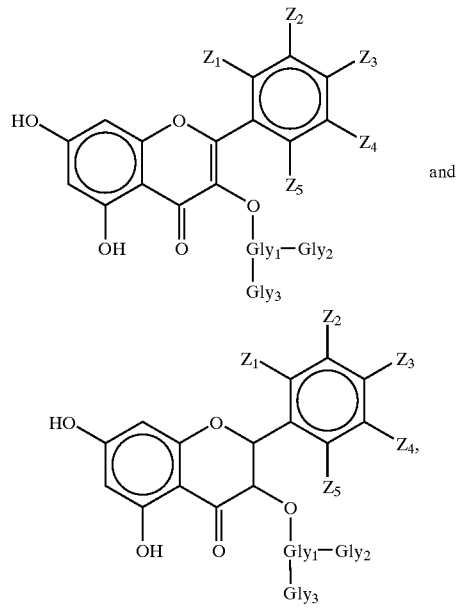

wherein $Z_1$–$Z_5$ have the abovementioned meaning and $Gly_1$, $Gly_2$ and $Gly_3$ are monoglycoside radicals.

Preferably, $Gly_1$, $Gly_2$ and $Gly_3$ independently of one another are chosen from the group consisting of hexosyl radicals or pentosyl radicals. Radicals such as allosyl, altrosyl, apiosyl, arabinosyl, ascorbinyl, biosidyl, galactosyl, gulosyl, glucosyl, glucoronidyl, idosyl, mannosyl, talosyl, dulcityl, fructosyl, mannityl, rhamnosyl, ribosyl, sorbityl and xylosyl are advantageously to be used. It is particularly advantageous to use rhamnosyl radicals or glucosyl radicals.

It is particularly advantageous in the context of the present invention to choose the flavone glycoside(s) from the group consisting of alpha-glucosylrutin, alpha-glucosylmyrictrin, alpha-glucosylisoquercitrin and alpha-glucosylquercitrin.

Compounds such as alpha-glucosylrutin, alpha-glucosylhesperidin, alpha-glycosylnaringin, alpha-mannosylrutin and alpha-rhamnosylrutin are moreover particularly preferred.

It may also be advantageous to choose one or more of the $Gly_1$, $Gly_2$ and $Gly_3$ radicals from the group consisting of oligo- or poly-α- or -β-glycosidic compounds, or from the group consisting of sugar acids or sugar esters. One or more $Gly_1$, $Gly_2$ and $Gly_3$ radicals can also be chosen from the group consisting of substituted sugars, such as, for example, N-acetylglucosamine.

It can also be of advantage to use flavonoids A) in which the glycoside radical is bonded to C7, C4', C3' or C5' via phenolic OH functions.

It may furthermore be of advantage to use flavonoids A) and glycosides thereof in which the phenolic OH function on C9 is present in the free form (so-called chalcones). In particular, it is advantageous to use neohesperidin dihydrochalcone from this group.

Particularly preferred flavonoids A) are: chrysin, naringin, hesperidin, naringenin, hesperetin, morin, phloridzin, diosmin, neohesperidin dihydro-chalcone, flavone and, in particular, alpha-glucosylrutin of the formula:

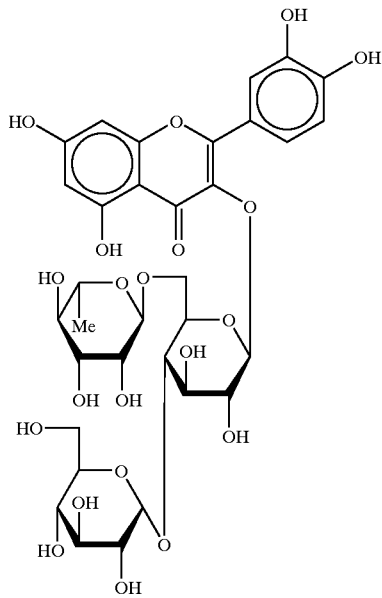

It may moreover be advantageous in the context of the invention to use commercially available flavonoid-containing plant extracts. These can be aqueous-alcoholic or aqueous-glycolic extracts obtained by the customary methods and also dry extracts.

Extracts which have proved to be particularly advantageous are: citrus fruit peel or kernel extract (for example Citricidal/Synthapharm), soya extract (for example Phytodermin/Chem. Laboratorium Dr. Kurt Richter GmbH), Sophora japonica extract (for example Sophorine/Solabia), Scotch thistle extract (for example Psoralen Silymarin/Mani GmbH Chemische Produkte), cat's-foot blossom extract, spinach extract and a mixed plant extract of passion flower, blackcurrants and vine leaves (AE Complex/Solabia) and calendula extract (Pot Marigold AMI watersoluble/Alban Muller).

Suitable cinnamic acid derivatives are, for example, hydroxycinnamic acids and derivatives thereof, it being possible for the derivatives to be, for example, those defined below.

According to the invention, cinnamic acid derivatives of the general formula

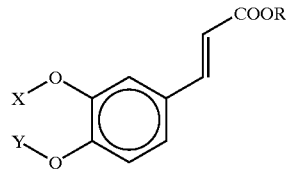

and/or active amounts of cinnamic acid derivatives of the general formula

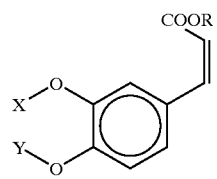

wherein the groups X, Y and R independently of one another can be chosen from the group consisting of H and branched and unbranched alkyl having 1–18 C atoms, in particular 1–6 C atoms, can preferably be used.

The acids or salts thereof, preferably the physiologically tolerated salts, for example water-soluble salts (sodium and potassium salts) can be used.

Ferulic acid is regarded as a particularly advantageous cinnamic acid derivative in the context of the present invention. Ferulic acid (4-hydroxy-3-methoxy-cinnamic acid, caffeic acid 3-methyl ether) is characterized by the structural formula

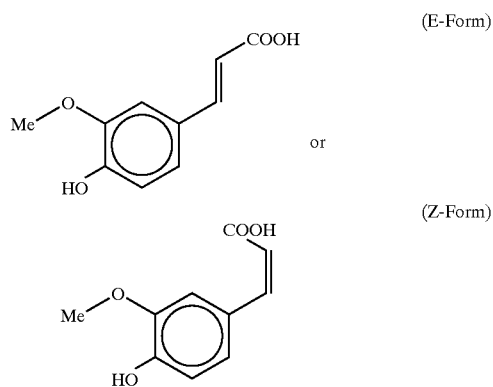

It is widespread in plants and occurs, for example, in beet crops, cereals and the latex of the umbelliferous plants Ferula asafoetida and Ferula nartex which give it its name. The E form is a colourless crystalline solid under normal conditions, and the Z form is a yellowish oil under normal conditions.

In the context of the present invention, it is preferable to use E-ferulic acid. However, it is also advantageous, where appropriate, to employ Z-ferulic acid or any desired mixtures of E- and Z-ferulic acid.

Another derivative of cinnamic acid which is preferred according to the invention is caffeic acid, which is distinguished by the structure

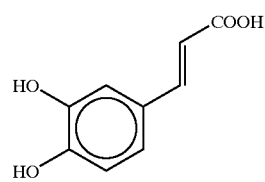

It is a widespread plant acid and is contained, for example, in coffee, tobacco, poppy and dandelion.

It is also advantageous, where appropriate, to use plant extracts with a content of cinnamic acid derivatives according to the invention, in particular ferulic acid and/or caffeic acid.

The term "derivatives of caffeic acid or ferulic acid" is to be understood as meaning their cosmetically or pharmacologically acceptable esters, salts and base adducts, in particular those such as are described above for the cinnamic acid derivatives.

Preferred combinations according to the invention are combinations of one or more substances from the group consisting of the abovementioned flavonoids or combinations of one or more representatives of the flavonoids with a derivative of cinnamic acid, or also the combination with several cinnamic acid derivatives.

The weight ratio of the cinnamic acid derivatives to the flavonoid or flavonoids is advantageously 25:1 to 1:25, preferably 5:1 to 1:5, particularly preferably about 2:1 to 1:2.

The combinations of flavonoids, flavone glucosides or flavonoid-containing plant extracts with ferulic acid and the combination of synthetically modified, in particular glycosylated flavonoids, such as alpha-glucosylrutin, with cinnamic acid derivatives are particularly preferred according to the invention.

Formulations with combinations b) which comprise alpha-glucosylrutin and/or ferulic acid are particularly preferred.

The compounds of group A or the combination of active compounds A) and B) can be present as the sole active compounds in the formulations according to the invention.

The cosmetic and dermatological formulations according to the invention preferably comprise 0.001% by weight to 30% by weight, preferably 0.01% by weight to by weight, but in particular 0.1% by weight to 6% by weight, based on the total weight of the formulation, of one or more substances A) according to the invention or of the combination of A) and B).

However, the formulations according to the invention can also preferably additionally have a content of an antioxidant or several antioxidants C), in addition to the active compounds A) or the combination of A) and B).

The antioxidants C) according to the invention can particularly advantageously be chosen from the group consisting of tocopherols and derivatives thereof. The tocopherols, also called vitamin E, are derived from the parent substance tocol ((2-methyl-2-(4,8,12-trimethyl tridecyl)chroman-6-ol). The configuration 2R,4'R,8'R is assigned to α-tocopherol, which occurs most frequently in nature and is the most important. It is occasionally also called RRR-α-tocopherol.

The tocopherol derivatives which are preferred according to the invention are α-tocopherol and its esters, in particular α-tocopheryl acetate. Esters of acids having 2 to 18, in particular 2 to 8 C atoms are preferred.

It is furthermore advantageous to use antioxidants C) from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal) chelators (for example α-hydroxy-fatty acids, palmitic acid, phytic acid or lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), vitamin A and derivatives (vitamin A palmitate) and coniferyl benzoate of benzoin resin, butylhydroxytoluene, butylhydroxyanisole, nordihydroguaiac resin acid, nordihydroguaiaretic acid, trihydroxybutyrophenone, uric acid and derivatives thereof, mannose and derivatives thereof, sesame oil, sesamolin, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of the abovementioned antioxidants C) (one or more compounds) in the formulations is preferably 0.001 to 30% by weight, particularly preferably 0.05–20% by weight, in particular 1–10% by weight, based on the total weight of the formulation.

The cosmetic and/or dermatological formulations according to the invention can have the customary comosition and can be used for the prophylaxis and/or treatment of the skin in the context of dermatological treatment or prophylaxis and/or treatment in the context of cosmetics. However, they can also be employed in make-up products in decorative cosmetics. They preferably comprise 0.001% by weight to 30% by weight, preferably 0.01% by weight to 10% by weight, but in particular 0.01% by weight to 6% by weight, based on the total weight, of one or more substances A) according to the invention or of the combination of A) and B).

It is advantageous according to the invention to use combinations of several substances according to the invention, in particular if at least one of the components is chosen from the group consisting of flavonoids or glucosides thereof and cinnamic acid derivatives.

It is particularly advantageous to use combinations of at least one compound from the flavonoids A) or derivatives thereof with at least one compound from the cinnamic acid derivatives B) and vitamin E or its derivatives C).

For use, the substances according to the invention and formulations according to the invention comprising such substances, preferably combinations of flavonoids or derivatives thereof, cinnamic acid derivatives and, if appropriate, antioxidants are applied to the skin in an adequate amount in the manner customary for cosmetics or dermatological agents.

Japanese Laid-Open Specification Hei-06-138,941 indeed describes oral formulations having a content of water-soluble glycosides, which can be chosen, for example, from the group consisting of α-glucosylrutin, α-glucosylmyrictrin, α-glucosylisoquercitrin and α-glucosylquercitrin. Japanese Laid-Open Specification Hei-04-363,395 describes a process for preventing decomposition of perfume constituents which is distinguished, inter alia, by an addition of α-glucosyl-rutin to the corresponding formulations. European Laid-Open Specification 586 303 and European Laid-Open Specification 595 694 furthermore describe the use of flavonoids as antioxidants or light protection substances in cosmetics. It is furthermore known from U.S. Pat. No. 4,144,325 and 4,248,861 and from numerous other documents to employ vitamin E in cosmetic and dermatological light protection formulations. The use according to the invention of vitamin E and its derivatives, however, was not made obvious by the prior art.

However, no indication which could lead in the direction of the present invention is to be found in these specifications.

It was therefore not foreseeable by the expert that the active compounds and active compound combinations according to the invention or cosmetic or dermatological formulations comprising these

- act better against ageing of the skin
- provide better protection for the lips
- better protect the skin and hair against photoreactions
- would better protect the hair and scalp during colouring of the hair and permanent waving
- better protect sensitive skin against unpleasant stinging
- are active against non-specific itching compared with the active compounds, active compound combinations and formulations of the prior art.

The invention therefore relates to the use of the active compounds or active compound combinations according to the invention for combatting and/or prophylaxis of ageing of the skin and inflammatory reactions caused by exposure to oxidation, and to the actions and uses mentioned above and below.

The invention therefore also relates to the use of cosmetic and dermatological formulations having a) a content of a compound or several compounds from the group consisting of flavonoids, or having b) a content of an active compound combination comprising a compound or several compounds chosen from the group consisting of flavonoids A) in combination with a compound or several compounds chosen from the group consisting of cinnamic acid derivatives and c) if appropriate an additional content of a compound or several compounds from the group consisting of antioxidants, for treatment and prophylactic treatment of ageing of the skin, for pretreatment or aftertreatment of the hair or scalp or of the hair root region, in particular before or after hair treatment, for example during colouring of the hair or permanent waving, for protecting the lips, in particular against exogenous noxae, for treatment and for prophylactic treatment of stinging or non-specific itching, for stabilizing or re-establishing the epidermal barrier function, for reducing or preventing damage to the skin and hair by oxidative influences, for protecting the skin or hair against photoreactions and for treatment or prophylactic treatment of the ageing of the skin and inflammatory reactions caused by exposure to oxidation.

Topical application is preferred for this use.

The cosmetic or dermatological formulations according to the invention can have the customary composition for these uses and can be used, for example, for the treatment, care and cleansing of the skin and/or hair and as a make-up product in decorative cosmetics. They preferably comprise 0.001% by weight to 30% by weight, preferably 0.01% by weight to 10% by weight, but in particular 0.1% by weight to 6% by weight, based on the total weight of the composition, of the active compounds according to the invention or their active compound combinations.

For use, the cosmetic and dermatological formulations according to the invention are preferably applied to the skin and/or hair in an adequate amount for cosmetics.

Cosmetic and dermatological formulations according to the invention can be in various forms. They can thus be, for example, a solution, an anhydrous formulation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or else an aerosol. It is also advantageous to administer the active compound combinations according to the invention in encapsulated form, for example encapsulated in collagen matrices and other customary encapsulating materials, for example as cellulose encapsulations, or in gelatin, wax matrices or liposomally. Wax matrices such as are described in DE-OS 43 08 282 have proved to be particularly favourable.

It is also possible and advantageous in the context of the present invention to introduce the active compound combinations according to the invention into aqueous systems or surfactant formulations for cleansing of the skin and hair.

The use of active compound combinations according to the invention for protection of the skin and/or hair against exposure to oxidation, in particular this use of the active compound combinations according to the invention in shampoos and washing formulations, is therefore also to be regarded as an advantageous embodiment of the present invention.

The cosmetic and dermatological formulations according to the invention can comprise cosmetic auxiliaries such as are usually used in such formulations, for example preservatives, bactericides, perfumes, substances for preventing foaming, dyestuffs, pigments which have a colouring action, thickeners, surface-active substances, emulsifiers, softening, humidifying and/or humectant substances, fats, oils, waxes or other customary constituents of a cosmetic or dermatological formulation, such as alcohols, polyols, polymers, foam stabilizers, electrolytes, organic solvents or silicone derivatives.

In particular, the formulations according to the invention can also comprise other antioxidants.

Favourable antioxidants which can be used according to the invention are all the antioxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homo-cysteine-sulphoximine, buthionine-sulphones and penta-, hexa- and heptathioninesulphoximine) in very low tolerated dosages (for example pmol to µmol/kg), and furthermore (metal) chelators (for example α-hydroxy-fatty acids, palmitic acid, phytic acid or lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, butylhydroxytoluene, butylhydroxyanisole, nordihydroguaiac resin acid, nordihydroguaiaretic acid, trihydroxybutyrophenone, uric acid and derivatives thereof, mannose and derivatives thereof, sesame oil, sesamolin, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of the abovementioned antioxidants (one or more compounds), which are not identical to the active compound combinations according to the invention, in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range from 0.001 to 10% by weight, based on the total weight of the formulation.

If vitamin A or vitamin A derivatives or carotenes or derivatives thereof are the antioxidant or antioxidants, it is advantageous to choose the particular concentrations thereof from the range from 0.001 to 10% by weight, based on the total weight of the formulation.

Emulsions according to the invention are advantageous and comprise, for example, the fats, oils, waxes and other fatty substances mentioned, as well as water and an emulsifier such as is usually used for such a type of formulation.

The lipid phase can advantageously be chosen here from the following group of substances:
  naturally occurring, synthetic and/or semi-synthetic oils, such as triglycerides of capric or caprylic acid, but preferably castor oil;
  fats, waxes and other naturally occurring synthetic and/or semi-synthetic fatty substances, preferably esters of fatty acids with alcohols of low C number, for example with isopropanol, propylene glycol or glycerol, or esters of fatty alcohols with alkanoic acids of low C number or with fatty acids;
  silicone oils, such as dimethyl polysiloxanes, diethyl polysiloxanes, diphenyl polysiloxanes and mixed forms thereof;
  saturated compounds, such as hydrocarbons of natural or synthetic origin (vaseline, squalane)

The aqueous phase of the formulations according to the invention advantageously comprises, where appropriate, alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol, and in particular one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of poly-acrylates, preferably a polyacrylate from the group of so-called Carbopols, for example Carbopols of types 980, 981, 1382, 2984 and 5984, or also of the ETD (easy-to-disperse) types 2001, 2020 and 2050, in each case individually or in any desired combinations with one another.

Mixtures of the abovementioned solvents are used in particular. In the case of alcoholic solvents, water can be a further constituent.

Gels according to the invention usually comprise alcohols of low C number, for example ethanol, isopropanol, 1,2-propanediol, glycerol and water, or an abovementioned oil, in the presence of a thickener, which is preferably silicon dioxide or an aluminium silicate in the case of oily-alcoholic gels and is preferably a polyacrylate in the case of aqueous-alcoholic or alcoholic gels.

Suitable propellants for formulations according to the invention which can be sprayed from aerosol containers are the customary known readily volatile, liquefied propellants, for example hydrocarbons (propane, butane, isobutane), which can be employed by themselves or as a mixture with one another. Compressed air can also advantageously be used.

Formulations according to the invention can furthermore advantageously comprise substances which absorb UV radiation in the UVB range, the total amount of filter substances being, for example, 0.1% by weight to 30% by weight, preferably 0.5 to 10% by weight, in particular 1.0 to 6.0% by weight, based on the total weight of the formulations, in order to provide cosmetic formulations which protect the hair or skin from the entire range of ultraviolet radiation. They can also be used as sunscreen agents for the hair or skin.

If the emulsions according to the invention comprise UVB filter substances, these can be oil-soluble or water-soluble. Oil-soluble UVB filters which are advantageous according to the invention are, for example:
  3-benzylidenecamphor derivatives, preferably 3-(4-methylbenzylidene)camphor and 3-benzylidene-camphor;
  4-aminobenzoic acid derivatives, preferably 2-ethylhexyl 4-(dimethylamino)-benzoate and amyl 4-(dimethylamino)benzoate;
  esters of cinnamic acid, preferably 2-ethylhexyl 4-methoxycinnamate and isopentyl 4-methoxycinnamate;
  esters of salicylic acid, preferably 2-ethylhexyl salicylate, 4-isopropylbenzyl salicylate and homomenthyl salicylate;
  derivatives of benzophenone, preferably 2-hydroxy-4-methoxybenzophenone, 2-hydroxy-4-methoxy-4'-methylbenzophenone and 2,2'-dihydroxy-4-methoxy-benzophenone;
  esters of benzmalonic acid, preferably di-(2-ethylhexyl) 4-methoxybenzalmalonate;
  2,4,6-trianilino-(p-carbo-$2^1$-ethyl-1'-hexyloxy)-1,3,5-triazine.

Advantageous water-soluble UVB filters are, for example:
  salts of 2-phenylbenzimidazole-5-sulphonic acid, such as its sodium, potassium or its triethanol-ammonium salt, and the sulphonic acid itself;
  sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and its salts.

The list of UVB filters mentioned, which can be used in combination with the active compound combinations according to the invention, is of course not intended to be limiting.

The invention also relates to the use of a combination of the active compounds according to the invention with at least one UVB filter as an antioxidant and to the use of a combination of the active compounds according to the invention with at least one UVB filter as an antioxidant in a cosmetic or dermatological formulation.

It may also be advantageous to combine active compounds according to the invention with UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and formulations which comprise these combinations. The amounts used for the UVB combination can be employed.

The invention also relates to the use of a combination of the active compounds according to the invention with at least one UVA filter as an antioxidant and to the use of a combination of the active compounds according to the invention with at least one UVA filter as an antioxidant in a cosmetic or dermatological formulation.

The invention also relates to the use of a combination of the active compounds according to the invention with at least one UVA filter and at least one UVB filter as an antioxidant and to the use of a combination of the active compounds according to the invention with at least one UVA filter and at least one UVB filter as an antioxidant in a cosmetic or dermatological formulation.

Cosmetic and dermatological formulations having an active content of active compounds according to the invention can also comprise inorganic pigments which are usually used in cosmetics for protecting the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide.

The invention also relates to these combinations of UVA filters and pigment and to formulations which comprise this combination. The amounts mentioned for the above combinations can be used.

Cosmetic and dermatological formulations for protecting the hair from UV rays in accordance with the invention are, for example, shampooing compositions, formulations which are used when rinsing the hair before or after shampooing, before or after permanent wave treatment or before or after colouring or bleaching the hair, formulations for blow-drying or setting the hair, formulations for colouring or bleaching, a styling and treatment lotion, a hair lacquer or a permanent wave composition.

The cosmetic and dermatological formulations comprise active compounds and auxiliaries such as are usually used for this type of formulation for hair care and hair treatment. The auxiliaries used are preservatives, surface-active substances, substances for preventing foaming, thickeners, emulsifiers, fats, oils, waxes, organic solvents, bactericides, perfumes, dyestuffs or pigments, the task of which is to colour the hair or the cosmetic or dermatological formulation itself, electrolytes and substances to prevent the hair becoming greasy.

Electrolytes in the context of the present invention are to be understood as meaning water-soluble alkali metal, ammonium, alkaline earth metal (including magnesium) and zinc salts of inorganic anions and any desired mixtures of such salts, where it must be ensured that these salts are distinguished by pharmaceutical or cosmetic acceptability.

The anions according to the invention are preferably chosen from the group consisting of chlorides, sulphates and hydrogen sulphates, phosphates, hydrogen phosphates and the linear and cyclic oligophosphates, and carbonates and bicarbonates.

Cosmetic formulations which are a skin cleansing composition or shampooing composition preferably comprise at least one anionic, nonionic or amphoteric surface-active substance or also mixtures of such substances, active compounds according to the invention in an aqueous medium and auxiliaries such as are usually used for this purpose. The surface-active substance or the mixtures of these substances can be present in the shampooing composition in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, they are, for example, aqueous or aqueous-alcoholic solutions which comprise, if appropriate, surface-active substances, the concentration of which can be between 0.1 and 10% by weight, preferably between 0.2 and 5% by weight.

These cosmetic or dermatological formulations can also be aerosols with the auxiliaries usually used for this purpose.

A cosmetic formulation in the form of a lotion which is not rinsed out, in particular a lotion for setting the hair, a lotion which is used for blow-drying the hair or a styling and treatment lotion, is in general an aqueous, alcoholic or aqueous-alcoholic solution and comprises at least one cationic, anionic, nonionic or amphoteric polymer or also mixtures thereof, as well as active compound combinations according to the invention in an active concentration. The amount of polymers used is, for example, between 0.1 and 10% by weight, preferably between 0.1 and 3% by weight.

Cosmetic formulations for the treatment and care of the hair which comprise active compounds according to the invention can be in the form of emulsions which are of the nonionic or anionic type. In addition to water, nonionic emulsions comprise oils or fatty alcohols, which, for example, can also be polyethoxylated or polypropoxylated, or also mixtures of the two organic components. If appropriate, these emulsions comprise cationic surface-active substances.

According to the invention, cosmetic formulations for the treatment and care of the hair can be in the form of gels which, in addition to an active content of active compound combinations according to the invention and solvents usually used for this purpose, preferably water, also comprise organic thickeners, for example gum arabic, xanthan gum, sodium alginate, cellulose derivatives, preferably methylcellulose, hydroxymethylcellulose, hydroxyethylcellulose, hydroxypropylcellulose or hydroxypropylmethylcellulose, or inorganic thickeners, for example aluminium silicates, such as, for example, bentonites, or a mixture of polyethylene glycol and polyethylene glycol stearate or distearate. The gel comprises the thickener, for example, in an amount of between 0.1 and 30% by weight, preferably between 0.5 and 15% by weight.

The amount of active compounds according to the invention in a composition intended for hair is preferably 0.05% by weight to 10% by weight, in particular 0.5% by weight to 5% by weight, based on the total weight of the composition.

Aqueous cosmetic cleansing compositions according to the invention or cleansing composition concentrates which are of low water content or anhydrous and are intended for aqueous cleansing can comprise anionic, nonionic and/or amphoteric surfactants, for example conventional soaps, for example fatty acid salts of sodium alkyl sulphates, alkyl ether-sulphates and alkane- and alkylbenzenesulphonates sulphoacetates sulphobetaines sarcosinates amidosulphobetaines sulphosuccinates sulphosuccinic acid half-esters alkyl ether-carboxylates protein-fatty acid condensates alkylbetaines and amidobetaines fatty acid alkanolamides polyglycol ether derivatives Cosmetic formulations which are cosmetic cleansing formulations for the skin can be in liquid or solid form. In addition to active compounds according to the invention, they preferably comprise at least one anionic, nonionic or amphoteric surface-active substance or mixtures thereof, if desired one or more electrolytes and auxiliaries such as are usually used for this purpose. The surface-active substance can be present in the cleansing formulations in a concentration of between 1 and 94% by weight, based on the total weight of the formulations.

Cosmetic formulations which are a shampooing composition preferably comprise, in addition to an active content of active compounds according to the invention, at least one anionic, nonionic or amphoteric surface-active substance or mixtures thereof, if appropriate an electrolyte according to the invention and auxiliaries such as are usually used for this purpose. The surface-active substance can be present in the shampooing composition in a concentration of between 1% by weight and 94% by weight.

In addition to the abovementioned surfactants, the compositions according to the invention comprise water and, if appropriate, the additives customary in cosmetics, for example perfume, thickeners, dyestuffs, deodorants, antimicrobial substances, agents which restore oils, complexing and sequestering agents, perlescent agents, plant extracts, vitamins, active compounds and the like.

The present invention also relates to a cosmetic process for protecting the skin and hair from oxidative or photooxidative processes, which is characterized in that a cosmetic composition which comprises an active concentration of active compounds according to the invention is applied to the skin or hair in an adequate amount.

The present invention also relates to a process for protecting cosmetic or dermatological formulations against oxidation or photooxidation, these formulations being, for example, formulations for the treatment and care of the hair, in particular hair colouring compositions, hair lacquers, shampooing compositions and colour shampooing compositions, and furthermore make-up products, such as, for example, nail varnishes, lipsticks, complexion foundations, washing and shower formulations, creams for the treatment or care of the skin or all the other cosmetic formulations, the constituents of which present stability problems during storage because of oxidation or photooxidation, characterized in that the cosmetic formulations comprise an active content of active compounds according to the invention.

The amount of active compounds according to the invention in these formulations is preferably 0.001% by weight to 10% by weight, in particular 0.01% by weight to 6% by weight, based on the total weight of the formulations.

The invention also relates to the process for the preparation of the formulations according to the invention, which is characterized in that active compounds according to the invention are incorporated into cosmetic and dermatological formulations in a manner known per se.

Unless stated otherwise, all the amounts data, contents and percentage contents are based on the weight and the total amount or on the total weight of the formulations.

The following examples are intended to illustrate the present invention without limiting it.

Example 1

| W/O cream | |
|---|---|
| | % by weight |
| Paraffin oil | 10.00 |
| Petrolatum | 4.00 |
| Wool wax alcohol | 1.00% |
| PEG 7-hydrogenated castor oil | 3.00 |
| Aluminium stearate | 0.40 |
| Rutin | 0.50 |
| Ferulic acid | 0.50 |
| Glycerol | 2.00 |
| Water, preservative and perfume to | 100.00 |

Example 2

| W/O lotion | |
|---|---|
| | % by weight |
| Paraffin oil | 20.00 |
| Petrolatum | 4.00 |
| Glucose sesquiisostearate | 2.00 |
| Aluminium stearate | 0.40 |
| Naringin | 1.00 |
| Ferulic acid | 0.25 |
| Vitamin E acetate | 2.00 |
| Vitamin C palmitate | 0.20 |
| Glycerol | 5.00 |
| Water, preservative and perfume to | 100.00 |

Example 3

| O/W lotion | |
|---|---|
| | % by weight |
| Paraffin oil | 8.00 |
| Isopropyl palmitate | 3.00 |
| Petrolatum | 4.00 |
| Cetearyl alcohol | 2.00 |
| PEG 40-castor oil | 0.50 |

O/W lotion

| | % by weight |
|---|---|
| Sodium cetearyl sulphate | 0.50 |
| Sodium carbomer | 0.40 |
| Hesperidin | 0.50 |
| Naringin | 0.20 |
| Ferulic acid | 0.25 |
| Glycerol | 3.00 |
| α-Tocopherol | 0.20 |
| Octyl methoxycinnamate | 5.00 |
| Butylmethoxydibenzoylmethane | 1.00 |
| Water, preservative and perfume to | 100.00 |

Example 4

O/W cream

| | % by weight |
|---|---|
| Paraffin oil | 7.00 |
| Avocado oil | 4.00 |
| Glyceryl monostearate | 2.00 |
| Sodium stearate | 1.00 |
| Caffeic acid | 0.50 |
| α-Glucosylrutin | 0.20 |
| Sodium phytate | 1.00 |
| Titanium dioxide | 1.00 |
| Sodium lactate | 3.00 |
| Glycerol | 3.00 |
| Water, preservative and perfume to | 100.00 |

Example 5

Lip care stick

| | % by weight |
|---|---|
| Hydrogenated castor oil | 4.00 |
| Ceresin | 8.00 |
| Beeswax | 4.00 |
| Carnauba wax | 2.00 |
| Petrolatum | 40.00 |
| α-Glucosylhesperidin | 1.00 |
| β-Carotene | 0.10 |
| Caffeic acid | 0.30 |
| Paraffin oil, pigments and dyestuffs to | 100.00 |

Example 6

Liposome-containing gel

| | % by weight |
|---|---|
| Lecithin | 6.00 |
| Shea butter | 3.00 |
| Ferulic acid | 0.50 |
| Chrysin | 0.10 |
| Vitamin A palmitate | 0.20 |
| Biotin | 0.08 |
| Sodium citrate | 0.50 |
| Glycine | 0.20 |
| Urea | 0.20 |
| Sodium PCA | 0.50 |

Liposome-containing gel

| | % by weight |
|---|---|
| Hydrolysed collagen | 2.00 |
| Xanthan gum | 1.40 |
| Sorbitol | 3.00 |
| Water, preservative and perfume to | 100.00 |

Example 7

Hair treatment course

| | % by weight |
|---|---|
| Paraffin oil | 3.00 |
| Almond oil | 3.00 |
| Cetostearyl alcohol | 5.00 |
| PEG 40-castor oil | 1.00 |
| Sodium cetearyl sulphate | 0.50 |
| Sorbitol | 5.00 |
| Glycerol | 5.00 |
| Ferulic acid | 0.50 |
| Citricidal | 0.80 |
| Dilauryl thiodipropionate | 0.05 |
| L-Arginine | 0.10 |
| Water, preservative and perfume to | 100.00 |

Example 8

Massage cream

| | % by weight |
|---|---|
| Stearyl alcohol | 2.00 |
| Petrolatum | 4.00 |
| Dimethicone | 2.00 |
| Isopropyl palmitate | 6.00 |
| Cetearyl alcohol | 4.00 |
| PEG 40-hydrogenated castor oil | 2.00 |
| Ferulic acid | 0.50 |
| α-Glucosylrutin | 0.30 |
| Glycerol | 3.00 |
| Water, preservative and perfume to | 100.00 |

What is claimed is:

1. A method for the treatment or prophylaxis of skin against aging and the inflammation of skin caused by exposure of the skin to oxidation or for protecting the skin and the hair from photoreactions which comprises applying an effective amount of a formulation comprising, a) α-glucosyl rutin, and b) one or more compounds selected from the group consisting of antioxidants to said skin or hair.

2. A method for the treatment or prevention of wrinkles in the skin, which comprises applying an amount effective therefor of a formulation comprising, a) α-glucosyl rutin, and b) one or more compounds selected from the group consisting of antioxidants to said skin or hair.

* * * * *